United States Patent [19]

Sick

[11] Patent Number: 4,625,666
[45] Date of Patent: Dec. 2, 1986

[54] OPTICAL THREAD BREAKAGE MONITORING APPARATUS FOR TUFTING MACHINES

[75] Inventor: Erwin Sick, Icking, Fed. Rep. of Germany

[73] Assignee: Erwin Sick GmbH Optik-Elektronik, Fed. Rep. of Germany

[21] Appl. No.: 808,961

[22] Filed: Dec. 13, 1985

[30] Foreign Application Priority Data

Dec. 31, 1984 [DE] Fed. Rep. of Germany ....... 3447869

[51] Int. Cl.$^4$ ............................................. D05C 15/00
[52] U.S. Cl. .................................. 112/273; 112/80.18; 112/278; 250/561
[58] Field of Search ...................... 112/273, 278, 79 R; 66/163; 250/561, 571; 200/61.18

[56] References Cited

U.S. PATENT DOCUMENTS

| | | | |
|---|---|---|---|
| 3,401,267 | 9/1968 | Engle et al. ........................... | 250/561 |
| 4,248,272 | 2/1981 | Wilson et al. ......................... | 250/561 |
| 4,293,776 | 10/1981 | Sick et al. ............................ | 250/572 |
| 4,311,916 | 1/1982 | Schenkel ............................. | 250/561 |
| 4,358,202 | 11/1982 | Puffer et al. ......................... | 250/571 |
| 4,538,536 | 9/1985 | Sick ..................................... | 112/273 |

*Primary Examiner*—Ronald Feldbaum
*Attorney, Agent, or Firm*—Townsend and Townsend

[57] ABSTRACT

An optical thread breakage monitoring apparatus for tufting machines contains a laser (36), a mirror wheel (17) which is illuminated by the laser and also a plurality of spaced apart strip-like deflecting mirrors (23, 11, 12) which direct the laser light which is cyclically deflected by the mirror wheel (17) onto a horizontally disposed concave mirror (13) which is arranged above the mirror wheel (17) and the deflecting mirrors (11, 12) and which forms the scanning beam (20''') which is directed towards the row of needles (14) of the tufting machine. A retroreflecting strip (15) is arranged behind the row of needles (14). The receipt of the light reflected from the retroreflecting strip (15) takes place in autocollimation (FIG. 1).

8 Claims, 1 Drawing Figure

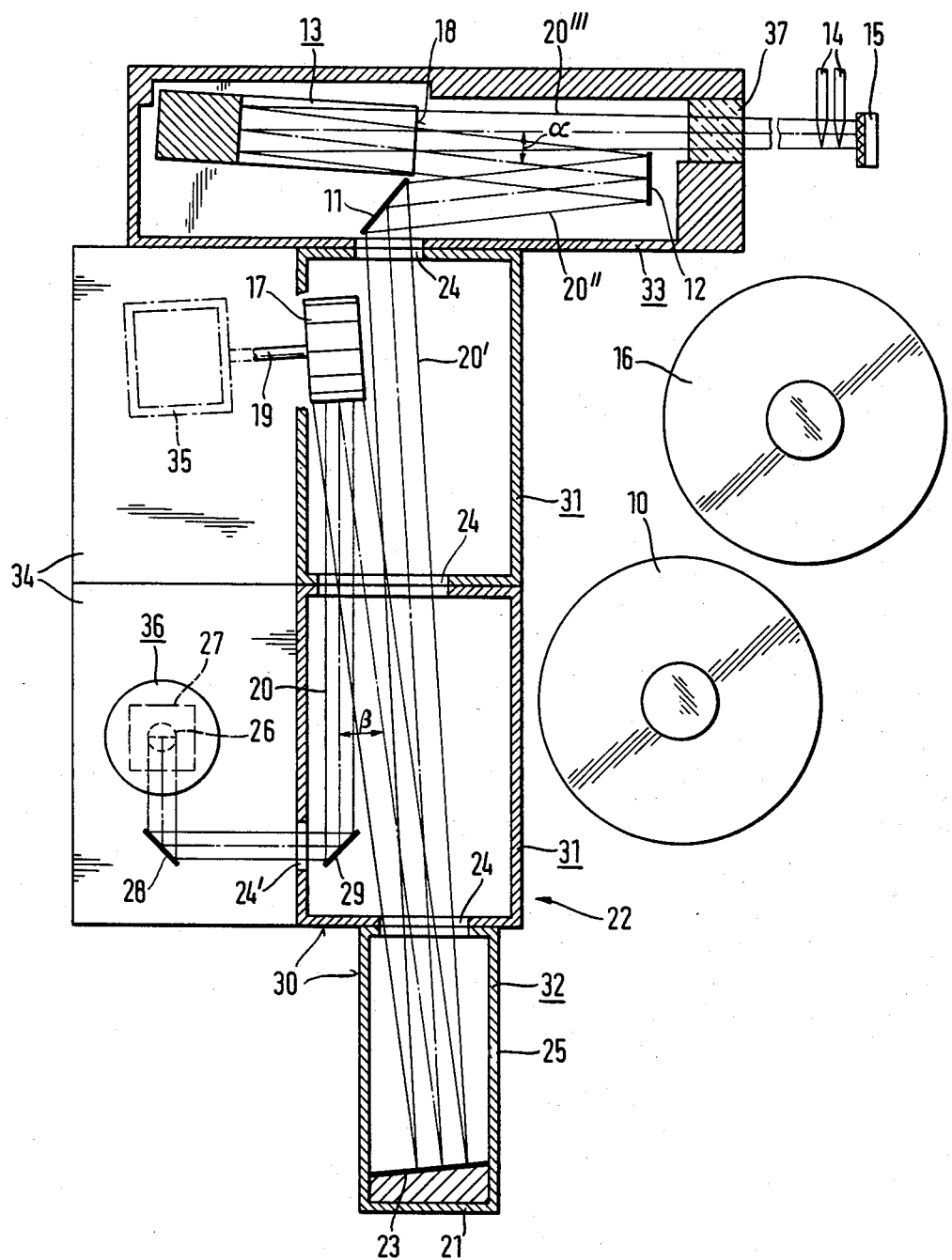

OPTICAL THREAD BREAKAGE MONITORING APPARATUS FOR TUFTING MACHINES

The invention relates to an optical thread breakage monitoring apparatus for tufting machines in which a carrier web is passed from below to a feed roller, is deflected by the latter into a substantially horizontal direction, and is then passed beneath a row of needles which periodically introduce threads into the carrier web by upward and downward movement for the formation of tufted material.

A known optical thread breakage monitoring apparatus for tufting machines is described in German Offenlegungsschrift DE-OS No. 33 31 772 and utilises a laser beam scanning device which has a narrow retroreflecting strip arranged immediately beneath and behind the needle tips when the needles are opened, immediately above and substantially perpendicular to the surface of the tufted material, and also parallel to the row of needles. The scanning device generates, by means of a mirror wheel and a strip-like concave mirror, a scanning beam in the form of a laser beam which periodically scans the retroreflecting strip and extends substantially parallel to the part of the carrier web which extends between the feed roller and the row of needles and perpendicular to the retroreflecting strip. The scanning device also includes a light receiver operating in autocollimation which is connected to an electronic fault evaluating circuit which, on the absence of a scanning beam interruption signal brought about by the needles and/or the threads extending between the needles and the carrier web, transmits a fault signal. The laser beam scanning device is vertically arranged in front of the feed roller and substantially below the level of the row of needles, and a strip-like deflecting mirror arranged substantially at the level of and parallel to the row of needles deflects the scanning beam which emerges substantially vertically out of the scanning device in the direction of the retroreflecting strip.

With this known thread breakage monitoring apparatus the problem exists that the operator, who is working in front of the machine, is hindered in the event of a thread breakage from effecting the required new placement of a torn thread by the relatively bulky thread breakage monitoring apparatus. A further disadvantage of the known apparatus lies in the fact that it can only embrace a relatively short region of the overall tufting machine, for example only a width of approximately 60 cm, so that for gapless cover of a 5 m wide tufting machine eight such prior known apparatuses must be arranged alongside one another. This is relatively involved and expensive.

The object underlying the invention is thus to provide an optical thread breakage monitoring apparatus which, as a result of a substantially more compact construction, enables the operator to have better access to the torn threads and at the same time however transmits a laser beam which is accurately directed to the row of needles or the retroreflecting strip. Moreover, it is an object of the present invention to provide thread breakage monitoring apparatus which can be made substantially wider without problem so that notably fewer apparatuses are necessary to cover a relatively broad tufting machine than is the case with the previously known apparatus.

This object is satisfied in an apparatus of the kind described above by an arrangement in which the first said deflecting mirror deflects the incident laser beam somewhat obliquely upwardly to a strip-like plane mirror extending parallel to it which deflects the laser beam upwardly to the concave mirror arranged on the opposite side of the first said deflecting mirror from the needle row, with the concave mirror being arranged parallel to and horizontally opposite to the needle row; and in which the mirror wheel is arranged directly below the first said deflecting mirror with its axis of rotation disposed somewhat tilted relative to the horizontal and receives the laser beam vertically from below and also directs the laser beam essentially downwardly, however somewhat obliquely in the direction of the row of needles to a further strip-like deflecting mirror arranged at the base of the housing near the wall facing the tensioning roller, with the further strip-like deflecting mirror extending parallel to the first said deflecting mirror and reflecting the laser beam upwardly past the mirror wheel to the first said deflecting mirror.

The advantage of the invention lies in the fact that the concave mirror is arranged closer to the field (needle plane) and thereby the focal length can be increased for a given volume of the housing relative to earlier arrangements. Moreover, the free space present in front of the feed roller is exploited for the beam path which leads to the concave mirror, which makes a further extension of the focal length of the mirror possible and thus an even greater width of the apparatus, i.e. an increase in the length of the scanned path.

The arrangement is preferably such that the strip-like plane mirror is arranged in a housing part which extends into the vicinity of, however not quite over the feed roller. The concave mirror is conveniently arranged directly above the first said deflecting mirror. In this embodiment the end edges of the concave mirror are substantially vertically aligned with the upper edge of the first said deflecting mirror facing the row of needles. In practice it is advantageous if the concave mirror has a length from 0.8 to 1.2 m, in particular of approximately 1 m, and afocal length of 0.8 m to 1.2 m and in particular of approximately 1 m, i.e. has a focal length equal to its length. Moreover, a particularly compact and stable arrangement is obtained if the mirror wheel, the first said deflecting mirror, the strip-like plane mirror and the strip-like concave mirror are accommodated in separate extruded housings of aluminium.

It is possible to supply several thread breakage monitoring apparatuses with a single laser beam generated from a laser source. This is achieved by an apparatus which is characterised in that the output laser beam extends parallel to the row of needles in the housing substantially beneath the concave mirror and is deflected by deflecting mirrors to the mirror wheel and also passes through a plurality of light apparatuses which are arranged alongside one another; and in that a partially transmitting deflecting mirror is provided in each apparatus which deflects out the part of the laser beam required for the relevant apparatus and permits the remaining part to pass on to the neighbouring apparatuses.

In this arrangement the laser beam preferably extends approximately at half the height of the housing; and the depth of the housing below the deflecting mirrors which are arranged close to the laser beam, is advantageously reduced abruptly via a step.

The invention will now be described in the following by way of example only and with reference to the drawing, the single FIGURE of which shows a cross-section perpendicular to the longitudinal extent of an optical thread breakage monitoring apparatus arranged at a tufting machine.

As seen in the drawing a housing 22 is arranged in front of the tensioning roller 10 and the feed roller 16 (which is preferably a spiked roller or toothed feed roller) and is put together from three extruded sections 31, 31 and 32 which are arranged above one another with a vertical front wall 25 at a relatively small distance from the tensioning roller 10. The upper two extruded sections 31 are of the same shape and are arranged aligned above one another, with a slot 24 for the passage of the beam being formed in the horizontal wall which is present between them. The bottommost extruded section 32 is of somewhat narrower shape and has, in the same way as the lower wall of the extruded section 31 which is located above it, a beam transmission slot 24. A deflecting mirror 23 is mounted at the bottom in the bottommost extruded section 32.

Box-like housing parts 34 are mounted on the side of the somewhat broader extruded aluminium sections 31 which faces away from the tufting machine. In the housing parts 34 there are arranged, at the top, the motor 35 (only shown in broken lines) for the mirror wheel 17 and at the bottom the laser beam 26 or the laser 36. The laser beam 26 extends horizontally and transverse to the tufting machine, i.e. perpendicular to the plane of the drawing, and impinges on a partially transmitting deflecting mirror 27 which deflects a part of the laser beam 26 downwardly to a deflecting mirror 28 which in turn deflects the laser beam horizontally to a further deflecting mirror 29 arranged inside the lower extruded section 31. An aperture 24' for the passage of the beam is provided for this purpose in the wall of the lower extruded section 31.

An extruded aluminium section 33 disposed with its major surface substantially horizontal is fixedly arranged on the uppermost extruded section 31 and, together with the substantially vertically arranged extruded sections 31, 32 forms a T-shaped arrangement. In other words the extruded section 33 projects both in the direction towards the tufting machine and also in the direction away from it significantly beyond the extruded sections 31, but not however beyond the housing parts 34.

The laser beam 20 which is directed vertically upwardly from the lower deflecting mirror 29 impinges on a mirror wheel 17 arranged in the top extruded section 31, with the axle of rotation 19 of the mirror wheel 17 being driven by the motor 35 and being slightly upwardly inclined relative to the horizontal in the direction towards the tufting machine. In this way the light reflected from the mirror wheel 17 is deflected obliquely downwardly to the mirror 23 which has a longitudinal extent perpendicular to the plane of the drawing such that the beam reflected from the mirror wheel 17 impinges in all rotational positions of the mirror wheel 17 on the strip-like mirror 23.

The mirror wheel 17 is located in the upper extruded section 31 as high as is permitted by the spatial construction of the arrangement, the plane mirror 23 is arranged as far down as possible, i.e. near to the floor.

The mirror wheel 17 is moreover arranged as close as possible to the wall of the extruded section 31 which faces away from the tufting machine so that adequate space remains on the opposite side for the reflected beam 20' which is reflected obliquely upwardly from the floor mirror 23 and which passes through the light transmitting slots 24 and impinges on a strip-like deflecting mirror 11 arranged in the uppermost extruded section 33, with the longitudinal axis of the deflecting mirror 11 extending perpendicular to the plane of the drawing.

The deflecting mirror 11 is arranged at an angle of approximately 50° to the horizontal so that it deflects the reflected beam 20'' which is directed somewhat obliquely upwardly to a strip-like plane mirror 12 which is accommodated at the end facing the tufting machine of the housing part 33 which projects towards the tufting machine. The housing part 33 extends approximately to the upper point of the feed roller 16, however terminates slightly in front of it. The inclination of the deflecting mirror 11 is selected so that the beam reflected from the strip-like mirror 12 can just pass above the deflecting mirror 11 where a strip-like concave mirror 13 with end edges 18 is arranged and which deflects the incident light in the direction of the row of needles 14 of the tufting machine, which is only schematically illustrated. A retroreflecting strip 15 is arranged behind the row of needles and extends perpendicular to the plane of the drawing. The receiving beam path is not shown but can be designed similarly to that of the apparatus of DE-OS No. 33 31 772, i.e. can operate in autocollimation.

In order that the travelling beam 20''' reflected from the concave mirror 13 can emerge from the upper hollow section 33 at one of its narrow sides a window 37 is provided in that narrow side.

Vibrational conditions (lack of vibration) favourable to a problem free beam path are obtained as a result of the relative proximity of the mirror wheel 17 and of the concave mirror 13 and also of the orthogonal arrangement of the longitudinal extent of the concave mirror 13 relative to the axis of rotation 19. Furthermore, as a result of the special arrangement of the mirror wheel and the concave mirror and of the double Z-beam path in the extruded sections 31, 32 on the one hand, and in the upper extruded section 33 on the other hand, it is possible to select a concave mirror 13 with a relatively large focal length, which makes it possible to make the concave mirror 13 relatively long in the direction perpendicular to the plane of the drawing, for example 1 m long. In this way the entire apparatus can be made relatively broad and a very large breadth of the tufting machine detected. For a 5 m long tufting machine only five pieces of apparatus in accordance with the invention need be arranged alongside one another in order to optically detect the entire row of needles 14.

The fact that only a simple Z-beam path is contained inside the housing means that the depth of the housing 22 and of the housing parts 24 arranged in front of it can be kept smaller than in the known apparatus, which sigifies that the operator can more easily reach the needle rows 14 in order to reset torn threads at this location.

The step-like projection 30 at the lower end has shown itself to be particularly favourable for a person sitting in front of the machine where, if necessary, the operators knees can be accommodated when sitting.

The subdivision of the housing 22 into three extruded aluminium sections 31, 31, 32 which are arranged above one another and the upper horizontally mounted further extruded section 33 results on the whole in a torsionally very stiff construction, so that for example with a load of 100 kp at 5 m a deflection of only 1 mm is produced.

It is particularly important that the length of the beams between the mirror wheel 17 and the concave mirror 23 is somewhat smaller than the focal length of the concave mirror 13, so the scanning beam 20''' emitted by the concave mirror 13 diverges somewhat outwardly at the ends of the scanning movement. This is important when several such apparatuses are arranged alongside one another in order to avoid scanning gaps between two pieces of apparatus. For this reason, the angle $\alpha$ of the Z-beam path within the upper extruded section 33 of approximately 6° should be approximately $\frac{1}{3}$ smaller than the angle $\beta$ of the Z-beam path in the housing 22 which amounts to 9°.

As a result of the proximity of the concave mirror 13 to the scanning field which is formed by the row of needles 14 the optical image formation of the light bead in this area is significantly improved.

The arrangement of all the optical elements in the hollow sections also brings the possibility of an improved seal against contamination.

In addition to the motor 35 for the mirror wheel 17 the electrical circuit components are also accommodated in the upper region of the housing parts 34.

I claim:

1. Optical thread breakage monitoring apparatus for tufting machines, in which a carrier web is passed from below to a feed roller and is deflected by the latter into a substantially horizontal direction to be passed beneath a row of needles which periodically introduce threads into the carrier web by upward and downward movement for the formation of tufted material, using a laser beam scanning device which has a narrow retroreflecting strip arranged immediately beneath and behind the needle tips when the needles are opened, immediately above and substantially perpendicular to the surface of the tufted material, and also parallel to the row of needles, wherein the scanning device generates, by means of a mirror wheel and a strip-like concave mirror, a scanning beam in the form of a laser beam which periodically scans the retroreflecting strip and extends substantially parallel to the part of the carrier web which extends between the feed roller and the row of needles and perpendicular to the retroreflecting strip, and contains a light receiver operating in autocollimation which is connected to an electronic fault evaluating circuit which, on the absence of a scanning beam interruption signal brought about by the needles and/or the threads extending between the needles and the carrier web, transmits a fault signal, wherein the laser beam scanning device is vertically arranged in front of the feed roller and substantially below the level of the row of needles, and wherein a strip-like deflecting mirror arranged substantially at the level of and parallel to the row of needles deflects the scanning beam which emerges substantially vertically out of the scanning device in the direction of the retroreflecting strip, characterised in that the deflecting mirror (11) deflects the incident laser beam somewhat obliquely upwardly to a strip-like plane mirror (12) extending parallel to it which deflects the laser beam upwardly to the concave mirror (13) arranged on the opposite side of the deflecting mirror (11) from the needle row (14), with the concave mirror (13) being arranged parallel to and horizontally opposite to the needle row (14); and in that the mirror wheel (17) is arranged directly below the deflecting mirror (11) with its axis of rotation disposed somewhat tilted relative to the horizontal and receives the laser beam (20) vertically from below and also directs the laser beam essentially downwardly, however somewhat obliquely in the direction of the row of needles (14) to a strip-like deflecting mirror (23) arranged at the base (21) of the housing (22) near the wall (25) facing the tensioning roller (10), with the strip-like deflecting mirror (23) extending parallel to the deflecting mirror (11) and reflecting the laser beam upwardly past the mirror wheel (17) to the deflecting mirror (11).

2. Apparatus in accordance with claim 1, characterised in that the strip-like plane mirror (12) is arranged in a housing part (extruded section 36) which extends into the vicinity of, however not quite over the feed roller (16).

3. Apparatus in accordance with claim 1, characterised in that the concave mirror (13) is arranged directly above the deflecting mirror (11).

4. Apparatus in accordance with claim 3, characterised in that the end edges (18) of the concave mirror (13) are substantially vertically aligned with the upper edge of the deflecting mirror (11) facing the row of needles (14).

5. Apparatus in accordance with claim 1, characterised in that the concave mirror (13) has a length from 0.8 to 1.2 m, in particular of approximately 1 m, and a focal length of 0.8 m to 1.2 m and in particular of approximately 1 m, i.e. has a focal length equal to its length.

6. Apparatus in accordance with claim 1, characterised in that the mirror wheel (17), the deflecting mirror (11), the strip-like plane mirror (12) and the strip-like concave mirror (13) are accommodated in separate extruded housings of aluminium (31, 32, 33).

7. Apparatus in accordance with claim 1, characterised in that the output laser beam (26) extends parallel to the row of needles (14) in the housing (22) substantially beneath the concave mirror (13) and is deflected by deflecting mirrors (27, 28, 29) to the mirror wheel (17) and also passes through a plurality of light apparatuses which are arranged alongside one another; and in that a partially transmitting deflecting mirror (27) is provided in each apparatus which deflects out the part of the laser beam (26) required for the relevant apparatus and permits the remaining part to pass on to the neighbouring apparatuses.

8. Apparatus in accordance with claim 7, characterised in that the laser beam (26) extends approximately at half the height of the housing (22); and in that the depth of the housing below the deflecting mirrors (27, 28, 29) which are arranged close to the laser beam, is reduced abruptly via a step (30).

* * * * *